United States Patent [19]

Schrems et al.

[11] Patent Number: 4,580,975
[45] Date of Patent: Apr. 8, 1986

[54] SET OF PREMANUFACTURED POSITIONERS FOR THE FINAL TREATMENT IN THE ORTHODONTIC AND JAW ORTHOPEDIC TOOTH ALIGNMENT

[76] Inventors: Hans T. Schrems; Gabriele Schrems-Adam, both of Dechbettener Strasse 1, D-8400 Regensburg 1, Fed. Rep. of Germany

[21] Appl. No.: 643,899

[22] Filed: Aug. 23, 1984

[30] Foreign Application Priority Data

Aug. 24, 1983 [DE] Fed. Rep. of Germany ....... 3330531

[51] Int. Cl.$^4$ .............................................. A61C 3/00
[52] U.S. Cl. ............................................................ 433/6
[58] Field of Search ............................................... 433/6

[56] References Cited

U.S. PATENT DOCUMENTS

| | | | |
|---|---|---|---|
| 3,478,429 | 11/1969 | Shilliday | 433/6 |
| 3,510,946 | 5/1970 | Kesling | 433/6 |
| 3,950,851 | 4/1976 | Bergersen | 433/6 |
| 4,370,129 | 1/1983 | Huge | 433/6 |
| 4,371,336 | 2/1983 | Hilleman | 433/6 |

FOREIGN PATENT DOCUMENTS

| | | | |
|---|---|---|---|
| 1616125 | 11/1979 | Fed. Rep. of Germany | 433/6 |
| 3232550 | 2/1984 | Fed. Rep. of Germany | 433/6 |

OTHER PUBLICATIONS

"Fortschritte der Kieferorthopaedie", 37, 1976, pp. 473 to 478.

Primary Examiner—John J. Wilson
Attorney, Agent, or Firm—Flynn, Thiel, Boutell & Tanis

[57] ABSTRACT

A fine alignment apparatus for the final treatment in orthodontic and jaw orthopedic tooth alignment, a so-called "positioner", has tooth receiving cavities (1,2). These cavities are recessed at the portions thereof away from the area which receives the incisal edges (4) of the incisors and canines (3) and the cusp tips (6, 7) of the side teeth (8). Through this position changes of the teeth when the positioner is inserted, which are caused by anatomic variations of the teeth or for example fillings, are reliably prevented.

10 Claims, 3 Drawing Figures

SET OF PREMANUFACTURED POSITIONERS FOR THE FINAL TREATMENT IN THE ORTHODONTIC AND JAW ORTHOPEDIC TOOTH ALIGNMENT

FIELD OF THE INVENTION

The invention relates to a set of premanufactured precision adjustment (fine alignment) apparati for the final treatment in the orthodontic/jaw orthopedic tooth alignment (tooth position adjustment).

BACKGROUND OF THE INVENTION

In orthodontic/jaw orthopedic treatment, bands, braces and removable appliances as functional appliances etc. are used to align the teeth or to bring them at least approximately into a predeterminable tooth position. In order to assure the treatment result achieved for example with bands or (since after the removing of the bands or braces there is a high instability of occlusion at a simultaneous optimum reactivity of the periodontal structures) in order to carry out small position corrections of the teeth (which cannot be carried out or can only be carried out with difficulties by the previously used apparati) after the bands are removed, precision adjustment apparati are inserted and are generally identified as "positioners".

Such positioners are formed individually either with the help of a so-called set-up-model (compare G. Schrems-Adam, H. Th. Schrems in "Fortschritte der Kieferorthopaedie" 37, 1976, Pages 473 to 478, translated English title: "Advances in the jaw orthopedics") or a set of few positioners of different size is premanufactured, which are dimensioned according to easily determinable parameters, namely either according to the total distance between two specific teeth of the jaw arch, which teeth lie symmetrically with respect to the jaw center, (German AS No. 16 16 125) or in consideration of the individual kinematics of the mandible according to the sum of the mesio-distal diameters of the teeth and according to the tooth arch form (German patent application No. P 32 32 550.9-35).

The tooth receiving cavities of the mentioned premanufactured positioners are thereby constructed such that they are very exactly adjusted to the outer contour of the teeth, so that the positioner snugly surrounds/rests on the teeth in the position which corresponds with the ideal set-up (ideal occlusion) position.

The tooth receiving cavities of individually manufactured positioners are constructed such that they are very exactly adjusted to the outer contour of the teeth, so that the positioner, after overcoming the incorrect tooth positions, finally snugly surrounds the teeth. The tooth receiving cavities of the mentioned premanufactured positioners are constructed such that they are very exactly adjusted to the outer contour of those teeth which were the basis for the original model during the creation of the ideal occlusion (set-up).

The outer entire contour of the teeth is, however, different from patient to patient, even with the same sum of the mesio-distal diameters of the teeth and the same tooth arch form.

Therefore, in practice when using the mentioned premanufactured positioners, there occurs the problem that, when the tooth receiving cavities of the positioner do not correspond with the outer contour of the teeth of the respective patient, an unintended position change of teeth relative to the desired ideal occlusion is caused.

The unintended position change is greater the more diligently the patient wears his positioner. From this results but a high recidivism danger, namely the danger of falling back into a similar situation as existed prior to the start of the treatment.

If for example the chewing surface of a tooth due to a filling has no longer a natural form, then the positioner, the receiving cavity of which for this tooth corresponds with the form of the natural grooves and fissures of the chewing surface, applies a specially large pressure onto the chewing surface of said tooth which has the filling. The result is that this tooth is pressed into the alveolar process more strongly than the other teeth, which causes an unintended position change of this tooth. This position change has an effect on the adjacent teeth and can lead like a chain reaction to position changes of many other teeth and thus again destroy the desired tooth and jaw arch form.

The structure and operating principle of the conventional individually manufactured and premanufactured positioners thus is based on the fact that the desired position change of the still incorrectly positioned teeth is effected by the positioner material which due to its elasticity under chewing pressure rests snugly on the entire outer surface of the teeth. This treatment phase can be identified as the active positioner phase, because here tooth movements are still being constantly carried out by the positioner.

If during the course of weeks or months, by correct wearing of the positioner, the teeth have been forced into their ideal position (set-up position), then the positioner is supposed to maintain this achieved ideal position. This treatment phase can be called the passive positioner phase, because tooth movements are no longer effected by the wearing of the positioner.

However, the experience shows that usually when mandibular kinematics are not considered when creating the set-up (which is common usage because of the high time and technical input required), the passive position of the maxillary and mandibular teeth, in which position they are held by the positioner, is not a functional one.

If the patient removes the positioner from the mouth, the maxillary and mandibular teeth meet differently than they meet in the positioner. Because of the complex relief structure of the occlusal surfaces, therefore premature contacts occur pointwise (merely at a point or points) on an individual tooth pair or on several tooth pairs during the first tooth contact in the hinge-axis closing-bit phase and thus individual teeth are overloaded and thus function-induced uncontrolled and uncontrollable deflections of the teeth occur, which finally lead to a chain reaction within the individual maxillary and mandibular tooth arches and between the tooth arches.

These tooth position changes take place within the tooth arches until, during the various functional and parafunctional loads, a load balance has occurred. In very many cases this load balance is not only achieved by tooth position changes which differ from the ideal treatment situation (set-up situation), but mainly by a compensatory misaligning (shifting) of the mandible relative to the maxilla. Thus one can differentiate between an alveolary compensation mechanism, which is caused by function, and a mandibulary (skeletal) compensation mechanism, which is also caused by function.

Furthermore experience shows that even in the case of maximum precision in treatment and in consideration of the individual kinematics of the mandible, only in exceptional cases is it possible to achieve the theoretically ideal set-up relationships in patients. Aside from technically caused errors in manufacture and material, it is mainly the impossibility of being able to sufficiently consider tissue behavior and tissue reaction that is responsible for this.

Therefore one can at most achieve a condition with the help of a precise orthodontic/jaw orthopedic therapy using the highest treatment precision, which condition comes close to the planned ideal condition. The last small position corrections of the teeth, which are necessary in order to assure optimum functioning and stable loading of all components, are carried out through natural compensation mechanisms, for example in the form of small tooth position changes or attritions by the organism itself. This individual adaptation operation can be identified as an individual settling-in.

Although it may be unjustified, this undesired position change of the teeth is often blamed on the patient by the treating person (dentist) for the reason that the patient is no longer wearing his treatment apparatus with the undesired position change as the necessary consequence.

Therefore, a method already has been disclosed which is supposed to secure a better retention. From German OS No. 26 08 797 it is known to apply a soft deformable material onto the positioner and to then insert the positioner into the mouth of the patient, after which the patient must close the teeth for a few minutes, until the applied material has become hard and has bonded with the base material of the positioner.

As stated above, however, such measures permit a prevention of unintended position changes of the teeth only so long as the apparatus is being worn subsequently. Just as in the case of the remaining known positioners, as soon as the apparatus of German OS No. 26 08 797 (which has been reset to function as a retention apparatus) is not worn and the teeth are "let go" on one another corresponding with functional conditions, the known consequence of undesired tooth position changes (recidiviation) occurs again, so that with this known apparatus is connected only an increased amount of work and a conserving effect, not, however, a long-time therapeutic effect.

Thus, it is also not possible with the positioner of German OS No. 26 08 797 to balance existing tooth form discrepancies between the patients' teeth and a premanufactured positioner, in order to achieve a better treatment effect of the premanufactured positioner. Here too is accomplished only a conserving effect on the just existing occlusion.

Mainly, however, the known positioner does not take any measures which concentrate on the respective terminal hinge axis position, or the ideal closing bite position, in which a maximum intercuspation in centric relation exists (centric relation occlusion). This has the result that, during biting into the known positioner, the condyles are strongly moved partly out of their fossae. After removing the known positioner there occurs therefore during intercuspation almost always a strong deflection of the condyles out of the fossae. This results in a strong mechanical influence on the joints and the neuromuscular system with mostly irreparable damage or consequent damage.

In other words, by using the conventional individually manufactured or premanufactured positioners, the tooth receiving cavities differ in form from the patients' tooth forms and/or have no function-coordinated set-up, and subsequent incorrect positions of the teeth thus always result, the latest after removal of the positioner.

The purpose of the invention is to produce a set of premanufactured positioners, which reliably maintains the result achieved by the orthodontic/jaw orthopedic treatment, without requiring additional work to be carried out on the premanufactured positioner.

This is achieved, under the present invention, by the tooth receiving cavities of the premanufactured positioner being constructed such that when the positioner is inserted, the pressure applied by the positioner onto the teeth is the greatest in the area of the occluding parts.

The basis of the present invention is thus the recognition that, with a specific tooth arch length and a specific tooth arch form, the positions of the cusp tips and incisal edges of the teeth (thus the positive occluding tooth parts) are practically identical in each patient, namely through the tooth arch length and the tooth arch form alone the position of these occluding tooth parts can be defined exactly. Variations of the teeth exist, however, in other anatomic respects and through specifically occurring tooth treatments.

In one anatomic respect, for example, when viewing the outer contour of the teeth in the gingival direction, the steepness of the side surfaces of the cusps and the side edges and the depth of the tooth grooves and fissures are different. During tooth treatment, for example, fillings must be considered.

Aside from the finding that, with a specific tooth arch length and tooth arch form, the position of the occluding parts of the teeth are defined exactly, the present invention furthermore is based on the recognition that, for holding of the teeth and for small position corrections, it is exclusively important that a force is applied on the occluding parts of the teeth. In contrast to the known positioners, in particular according to German AS No. 16 16 125 and German OS No. 26 08 797, it is thus not necessary that the positioner rest will all sides of its tooth receiving cavities fixedly against the teeth in order to securely hold the teeth.

This means that the nonoccluding parts of the teeth, which as mentioned can have different forms (with the same tooth arch length and tooth arch form) in anatomic respect and through specific tooth treatments, do not need to be exposed to any load, so that the tooth receiving cavities can be recessed or constructed very flexibly in the area thereof provided for receiving the nonoccluding parts of the teeth.

These recesses in the receiving cavities of the positioner in the area of the grooves and fissures of the teeth, also prevent, for example, the aforedescribed position change which occurs in the known positioner due to a tooth provided with a filling. It is also true that these recesses in the receiving cavities permit a greater contour of the teeth, in particular in labial and lingual direction.

Expressed differently, in the present invention use is made of the recognition that in a positioner, by building in of certain tolerances at points which are of subordinate importance or even unimportant for reciprocal stabilization of the tooth arches within themselves or between one another, no negative effects on the therapeutic result are to be expected.

The stabilization of the tooth arches with respect to one another is assured by the occluding parts, namely, the cusp tips and fissures (grooves) or enamel ridges. The occluding parts and here in particular the supporting cusp tips—in the maxilla these are the palatal cusp tips and in the mandible the buccal cusp tips—are for a predetermined tooth arch and jaw arch length almost constant to one another in their spacial position, independent of morphologic variations of the individual teeth. They furthermore have the advantage that dental therapy as fillings etc. have not as yet been carried out on them, especially at a child's age. They thus represent the best possible point of engagement for a premanufactured positioner. Also suited as a point of engagement are all parts which participate in occlusion, namely the incisal edges of the canines and incisors. However, they have the disadvantage of a high morphological variance and already have surface changes (abrasions) even at a child's age, which are caused by functional or parafunctional and malocclusion-caused overloads. They must then be timely compensated by grinding methods.

In case of the existence of tooth and jaw misalignments, the approach to the planned ideal condition (occlusion) has to occur thus with the help of known orthodontic/jaw orthopedic treatment devices.

It is now important to note that for the last fine corrections, which however are of the greatest importance for a stable function (treatment result), taking into consideration the individual kinematics of the mandible, so far satisfactory results have been achieved only with the known individually manufactured (custom made for each individual) positioners. Since the manufacture of such an individualized positioner however requires an almost unjustifiably large expense and with such an individualized positioner only a best possible approximation to the desired ideal situation can be achieved, the final definite adjustment must be done by the organism itself. A premanufactured positioner embodying the present invention is therefore disclosed hereafter, the operational effectiveness of which is based on the cusp tips (preferably the carrying cusp tips and the incisal edges of the teeth) as being the least changeable reference points of the set of teeth.

With this it is possible to achieve an optimum approximation to the ideal occlusion under varying morphologic conditions. The approximation effect with the inventive positioner is (according to experience to date) at least as great and often even better than with an individually manufactured positioner. The individual adaptation capability is stressed only to a minimum by the use of the inventive apparatus and is by no means overstressed. Unintended position changes of the teeth, which happen almost always when using premanufactured positioners because of the morphologic variance, are substantially and reliably prevented.

A further advantage is that the inventive positioner is able to make visible on time the causes (for example incorrect occlusal surface design due to fillings) of the creation of recidiviation, assuming that the correct position was chosen from the set using the known selection criteria (sum of the mesio-distal diameter of the teeth and tooth arch form of the patient).

BRIEF DESCRIPTION OF THE DRAWINGS

One embodiment of the inventive positioner will be discussed in greater detail hereinafter in connection with the drawing, in which.

DETAILED DESCRIPTION

Figure 1:
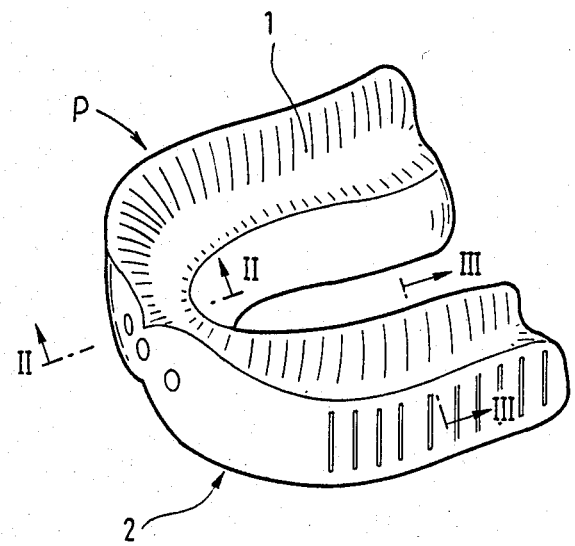
FIG. 1 is a perspective view of a positioner embodying the invention.
Figure 2:
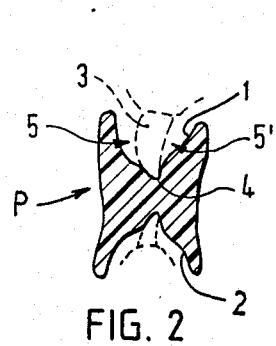
FIGS. 2 and 3 are cross-sectional views of the positioner according to FIG. 1 along the line II—II or III—III.

A positioner P has according to FIG. 1 a groove-shaped receiving cavity 1 for the maxillary teeth and a generally similar groove-shaped receiving cavity 2 for the mandibular teeth, which cavity 2 is visible in FIG. 2.

The respective lengths of the receiving cavities 1 and 2 of a given positioner P correspond to a specific sum of the mesio-distal diameter of all teeth of the maxilla and the mandible, respectively. Also, such given positioner P has a specific tooth arch form, which correspond to one of the three main tooth arch forms (see Ricketts "Design of Arch Form and Details for Bracket Placement" 1979, published by Rocky Mountains/Orthodontics).

As can be seen from FIG. 2, the portion of the tooth receiving cavity 1 near the incisor 3 is constructed such that it rests snugly against the area of the incisor 3 including and adjacent to the incisal edge 4, but is recessed in its remaining areas 5, 5', to be spaced from the area of the tooth flanks of the incisor 3.

This measure makes possible the utilization of the premanufactured positioner for different morphological structure of the incisors mainly in the buccal-palatal (buccal-lingual) direction.

Figure 3:
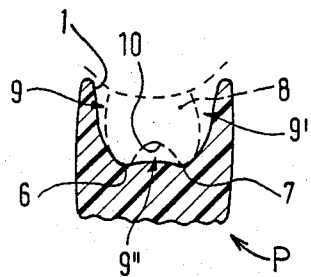

According to FIG. 3 the tooth receiving cavity 1 rests snugly against the area of the molars 8 including and adjacent the cusp tips 6 and 7 on such molars 8, but is recessed in its remaining areas 9, 9', 9" to be free of contact with opposed areas of the molar 8, even despite considerable variation in the shape of different molars 8, for example in the lingual or labial direction. Also, in the area 9" contact with the molar 8 is impossible even when the molar cavity 10 contains a filling which is too high, which filling is thus wrong because it changes occlusion.

The inventive positioner P in its tooth receiving cavities 1 and 2 thus applies pressure on only the occluding parts of the teeth, namely the incisal edges of the incisors and canines and the cusp tips of the side teeth (premolars and molars), while the remaining areas of the tooth receiving cavities 1, 2 (namely those areas outside the area receiving the occluding parts of the teeth and thus namely the areas 5, 5' and 9, 9', 9") are recessed away from the teeth.

The receiving cavities 1 and 2 are preferably also recessed away from the teeth in the area of the interproximal spaces thereof.

The recessing of the tooth receiving cavities 1 and 2 can thus include the entire area therein except for the area therein receiving the occluding parts of the teeth. Alternately, such recessing can also be made only partial, in order to favor desired tooth movements and to exclude undesired tooth movements. In the maxilla, for example in the side tooth area mainly, the mesial interproximal septs are obtained relatively precisely, whereas they almost do not exist in the distal area up to the interproximal line, because with this a distalisation effect or a reinforced retention of the teeth in distal direction is effected. In the mandibular side tooth area, where often a mesial movement is desired, the shaping of the interproximal septs is carried out exactly in reverse. It can even appear to be advantageous not to provide any individual tooth-tooth cavities, but rather to provide fields for individual tooth groups, for example for the front tooth group, premolar group and molar group, with different distinctive fixation, because often individual tooth size variations which differ from the norm are compensated for.

Decisive for a best possible positioner function is mainly that, with the help of the receiving cavities, the tooth arch length specific (individual tooth arch length) and jaw arch length specific arch characteristic (individual jaw arch length) is detected in consideration of the kinematics of the mandible.

Instead of the recesses, the inventive positioner can also have tooth receiving cavities which in the area for receiving the occluding parts of the teeth have a material with a lower elasticity than in the area of the nonoccluding parts of the teeth. The elasticity of the material can thereby gingivally progressively decrease from the area for receiving the occluding parts of the teeth.

Instead the tooth receiving cavities can also be constructed such that they have, outside of the area for receiving the occluding parts of the teeth, a plastically deformable material.

Important is only that the occluding parts of the teeth, namely the incisal edges of the incisors and the canines and the cusp tips of the side teeth, are at all times fixed at an optimum position, namely the tooth arch length specific and jaw arch length specific arch characteristic is sufficiently fixed by a suitable covering (fixation) of the teeth.

The inventive positioner can for example be manufactured as follows:

Upper and lower models with ideal tooth positioning and with ideal joint relationships are constructed. The models are blocked out in the area of the grooves and fissures with wax and by waxing up the individual tooth types are each approximated to the largest tooth form which exists according to a statistical distribution or which is found by tooth selection. The casts are tested using an articulator (full adjustable instrument) regarding disadvantageous effects through the application of wax with respect to occlusion and the joint relationships. It is then covered with a deep-drawing foil (plate), in order to obtain an even and smooth surface. An impression is then taken from the deep-drawn model and from the impression is then manufactured a special model for creating the premanufactured positioner.

For this successful use of the inventive positioner, it is of course necessary to test all occluding surfaces, including negative going occlusal surfaces (grooves etc.), which are often changed by dental treatment. If necessary, a revision of the occlusal surfaces, which are changed by dental treatment, must occur by grinding away excessively applied filling material which no longer corresponds with the original tooth surface. Of course, also necessary is a checking of mesio-distal length changes, which may possibly be caused by fillings. These lastmentioned tests are, however, basically necessary for the successful utilization of any orthodontic/jaw orthopedic treatment devices.

We claim:

1. A set of premanufactured precision adjustment apparati for the final treatment in orthodontic/jaw orthopedic tooth position adjustment in patients, a said apparatus being of an elastic material, each apparatus having flanges covering essentially the whole area of the buccal and lingual surfaces of the teeth and having cavities receiving the incisors, canines and side teeth, the length of which cavities are measured to correspond with the statistical distribution of mesio-distal tooth diameters of the patients, the precision adjustment apparati of the set covering substantially the entire jaw and tooth size range which occurs in patients, the tooth receiving cavities being constructed such that the tooth receiving cavities have first means for maximizing the load applied thereby to cusp tips of the side teeth and the incisal edges of the incisors and canine teeth and second means for minimizing the load applied by said tooth receiving cavities to all other portions of said teeth, said first means constituting localized first areas of said cavities receiving said cusp tips of the side teeth and said incisal edges of the incisors and canine teeth, said second means constituting areas of said cavities other than said first areas.

2. A precision adjustment apparatus set according to claim 1, wherein the tooth receiving cavities correspond with the dimensions of the respective teeth which have a specific mesio-distal diameter, which dimensions are the largest occurring according to a statistical distribution.

3. A precision adjustment apparatus set according to claim 1, wherein the tooth receiving cavity areas, other than said first areas, flank the buccal and lingual surfaces of the teeth but are recessed away from said buccal and lingual surfaces of the teeth.

4. A precision adjustment apparatus set according to claim 1, wherein the tooth receiving cavity areas, other than said first areas, flank the buccal and lingual surfaces of the teeth but are of a material of a greater elasticity than in said first areas.

5. A precision adjustment apparatus set according to claim 4, wherein the material of lesser elasticity is irreversibly deformed during an unphysiological overload of the teeth by the acting chewing force.

6. A precision adjustment apparatus set according to claim 4, wherein the elasticity of the material slowly decreases gingivally from the area for receiving at least one of the occluding parts of the teeth and the incisal edges of the front and canine teeth and the cusp tips of the side teeth.

7. A precision adjustment apparatus set according to claim 1, wherein the tooth receiving cavity areas, other than said first areas, flank the buccal and lingual surfaces of the teeth and are of a plastically deformable material.

8. A precision adjustment apparatus set according to claim 1, wherein the design of the tooth receiving cavities is modified in dependency from the various angle classes.

9. A set of premanufactured precision adjustment apparati for the final treatment in orthodontic/jaw orthopedic tooth position adjustment, a said apparatus consisting of an elastic material, each apparatus having flanges covering essentially the whole area of the buccal and lingual surfaces of the teeth, each apparatus having cavities receiving the incisors, canines and side teeth, the length of which cavities are measured to correspond with the statistical distribution of mesio-distal tooth diameters of the patients, the precision adjustment apparati of the set covering substantially the entire jaw and tooth size range which occurs in patients, the tooth receiving cavities being constructed such that the tooth receiving cavities have localized contact areas for abutting the cusp tips of the side teeth and the incisal edges of the incisors and canine teeth, the tooth receiving cavities being recessed away from said teeth outside of said contact areas thereof abutting the cusp tips of the side teeth and the incisal edges of the incisors and the canine teeth.

10. A set of premanufactured precision adjustment apparati for the final treatment in orthodontic/jaw orthopedic tooth position adjustment, a said apparatus consisting of an elastic material, each apparatus having flanges covering essentially the whole area of the buccal and lingual surfaces of the teeth, each apparatus having cavities receiving the incisors, canines and side teeth, the length of which cavities are measured to correspond with the statistical distribution of mesio-distal tooth diameters of the patients, the precision adjustment apparati of the set covering substantially the entire jaw and tooth size range which occurs in patients, the tooth receiving cavities being constructed such that the tooth receiving cavities have localized contact areas for abutting the cusp tips of the side teeth and the incisal edges of the incisors and the canine teeth, which localized contact areas are made of a material of a lesser elasticity than the other areas of the cavities.

* * * * *